US006534001B1

(12) United States Patent
Michael et al.

(10) Patent No.: US 6,534,001 B1
(45) Date of Patent: Mar. 18, 2003

(54) FLUID IRRADIATION SYSTEM WITH LAMP HAVING AN EXTERNAL DRIVE COIL

(75) Inventors: Joseph Darryl Michael, Clifton Park, NY (US); Bruce Edward Brackett, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/351,894

(22) Filed: Jul. 13, 1999

(51) Int. Cl.[7] .............................. A61L 2/00; B01J 19/08; B01D 15/00; B01D 17/06; G01N 21/01
(52) U.S. Cl. .................. 422/24; 422/4; 422/186.04; 422/186.21; 422/186.29; 422/186.3; 422/305; 250/432 R; 250/435; 210/198.1; 210/205; 210/748
(58) Field of Search .................... 422/1, 5, 22–24, 422/186.04, 186.21–186.22, 186.29, 186.3, 187–188, 305, 308, 905–907; 250/432 R, 435; 210/198.1, 205, 748

(56) References Cited

U.S. PATENT DOCUMENTS

| 4,251,234 A | * | 2/1981 | Chang |
| 4,783,615 A | * | 11/1988 | Dakin |
| 4,910,439 A | * | 3/1990 | El-Hamamsy et al. |
| 5,247,178 A | * | 9/1993 | Ury et al. |
| 5,382,878 A | * | 1/1995 | Secen et al. |
| 5,691,598 A | * | 11/1997 | Belle et al. |

* cited by examiner

Primary Examiner—Robert J. Warden, Sr.
Assistant Examiner—Monzer R. Chorbaji
(74) Attorney, Agent, or Firm—Toan P. Vo; Noreen C. Johnson

(57) ABSTRACT

The invention relates to an irradiation system for disinfecting water comprising a conduit which is transparent to ultraviolet radiation, a chamber having an annular cross section, disposed around the conduit, the chamber containing an ionizable gas, and a coil disposed around the chamber for ionizing the ionizable gas to produce an ultraviolet emission which propagates into the conduit to disinfect the water flowing through the conduit.

28 Claims, 4 Drawing Sheets

FLUID IRRADIATION SYSTEM WITH LAMP HAVING AN EXTERNAL DRIVE COIL

BACKGROUND

1. Field of the Invention

The present invention relates generally to an irradiation system, and more particularly to a water disinfection system comprising an electrodeless UV lamp with an external drive coil.

2. Description of the Related Art

Conventional water disinfection systems typically include an elongated ultraviolet (UV) lamp which projects UV radiation radially outwardly into a surrounding water flow passage. As the water flows through the flow passage, the UV radiation kills harmful bacteria and microbes in the water. The flow passage typically has an annular cross section, defined on the inside by a transparent sleeve which surrounds the UV lamp, and on the outside by an opaque cylindrical container which contains the water and prevents UV radiation from escaping from the system.

In the conventional water disinfection system, the lamp typically comprises a linear low pressure discharge lamp which includes two electrodes inside a glass envelope. Each electrode typically comprises a tungsten coil coated with the oxide of an alkaline earth element such as barium, strontium, or calcium. The alkaline earth oxide is provided on the tungsten wire to increase the thermionic emission of electrons at the cathode. The lamp is very similar to a conventional fluorescent lamp, except that there are no phosphor coatings, and the glass envelope transmits a substantial amount of the UV radiation.

Glass provides the advantage that the electrical leads to the electrodes can be sealed relatively easily in a gas-tight manner with the glass in a softened state. The glass envelope, however, becomes solarized over time from exposure to the UV flux. Solarization is typically exhibited as a darkening of the envelope and results in increased absorption of UV radiation. After a certain period of use, the glass lamp typically must be replaced due to solarization.

The electrodes also have a relatively short lifetime, because the alkaline earth oxide material is depleted over time, as in a conventional fluorescent lamp, primarily by evaporation. After the alkaline earth oxide is depleted, the lamp will either fail to start or will enter a glow discharge state during operation, which quickly sputters away the remaining cathode material. In addition, the electrodes in such a lamp can support only a limited power output, thus limiting the disinfection capability of the device.

It would be desirable, therefore, to have a water disinfection system which was more robust than conventional systems with a greater lifetime and higher available operating power.

SUMMARY

An irradiation system, according to an exemplary embodiment of the invention, comprises a conduit which is transparent to ultraviolet radiation, a chamber having an annular cross section, disposed around the conduit, the chamber containing an ionizable gas, and a coil disposed around the chamber for ionizing the ionizable gas to produce an ultraviolet emission which propagates into the conduit.

The invention also relates to an irradiation method comprising the steps of generating a UV emission in a chamber having a conduit passing through the chamber, the conduit being fluidly isolated from the chamber, and flowing a fluid through the conduit such that the fluid is exposed to the UV emission generated in the chamber.

The invention provides several advantages over conventional UV water disinfection systems. For example, the lamp portion of the system has no electrodes which allows the system to operate at a higher power and over a longer lifetime than conventional water disinfection systems. The electrodeless design of the lamp also provides the advantage that there are no electrical leads passing through the walls of the chamber 130 so that the chamber 130 can be easily made of quartz, which is much less susceptible to solarization and has good UV transmission properties. An additional advantage provided by exemplary embodiments of the invention is the ability to easily install multiple lamps in a system in accordance with the desired power for the system.

BRIEF DESCRIPTION OF THE DRAWINGS

Other features and advantages of the invention will be more readily understood upon reading the following detailed description, in conjunction with the drawings, in which.

DETAILED DESCRIPTION OF THE PREFERRED EMBODIMENTS

Figure 1:
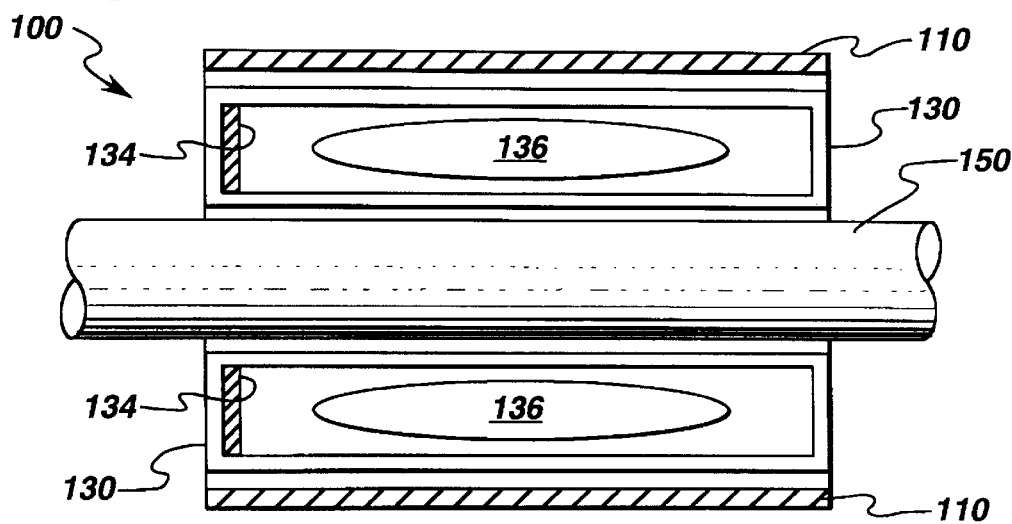
FIG. 1 is a cross sectional view of a fluid irradiation system comprising a single-turn coil according to an exemplary embodiment of the invention.

Referring to FIG. 1, a water disinfection system is shown in cross section according to an exemplary embodiment of the invention. The system 100 includes a coil 110, a chamber 130, and a conduit 150. The system 100 may be used to disinfect water containing bacteria or microbes, for example. The coil 110 and the discharge chamber 130 together constitute what is referred to as an "electrodeless" lamp, since there are no electrodes in the discharge chamber.

Figure 2:
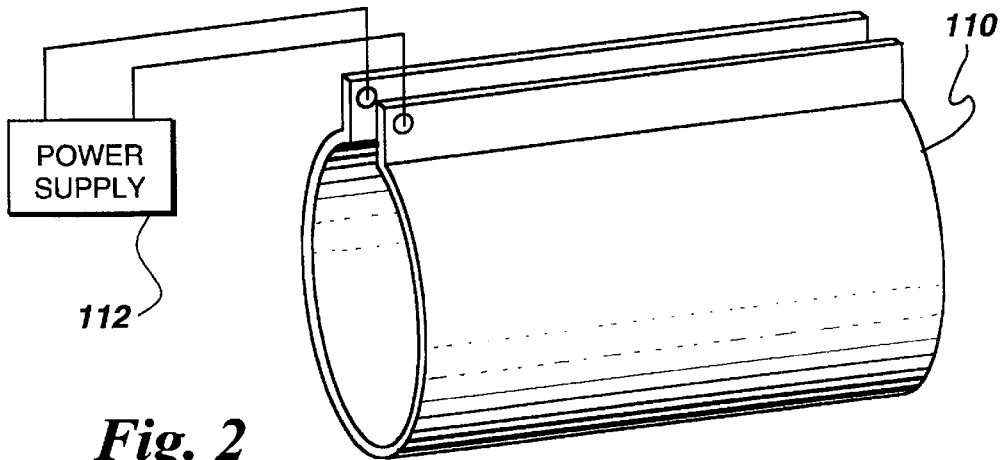
FIG. 2 is a drawing of the coil and associated electronics according to an exemplary embodiment of the invention.

The coil 110, according to one embodiment of the invention, is in the form of a single turn conductive member. The coil is generally cylindrical and typically comprises a metal such as aluminum or copper, for example. The coil 110 functions to generate an electric field from an oscillating magnetic field in the chamber 130. The coil 110 also functions to reflect light toward the centrally located conduit 150. The coil 110 is shown in perspective view in FIG. 2. Typically, the coil has an axial length of about 5–25 cm, a diameter of about 5–25 cm, and a thickness of about 1–2 mm. The coil 110 may have an axial length which is less than 2 times its diameter, according to one embodiment of the invention. As will be recognized by those skilled in the art, a coil having multiple turns can also be used in conjunction with exemplary embodiments of the invention.

The coil is powered by a power supply 112 which typically includes an oscillator which oscillates at radio frequencies (RF), typically about 1–100 MHz, more typically 13.56 MHz. The power supply 112 may provide a relatively low level of power to the coil, e.g. 20–40 watts, or may provide a higher power, e.g. at or above 50, 100, 150, or 200 watts. The lamp is able to operate at relatively high powers in part because the power is supplied via the coil 110 rather than by electrodes inside the discharge chamber as in a conventional system. The oscillator includes a rectifier which supplies a DC voltage and which receives a conventional 60 Hz 120 volt AC input voltage. An impedance matching network can be provided between the oscillator and the coil 110 for efficient energy coupling into the discharge chamber.

Figure 3:
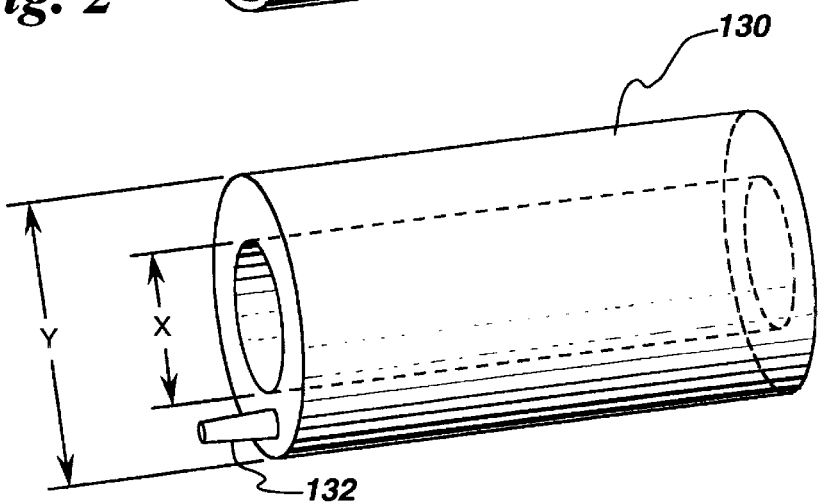
FIG. 3 is a drawing of an exemplary discharge chamber.

Referring again to FIG. 1, the coil 110 is disposed around the discharge chamber 130. FIG. 3 shows a perspective view of the discharge chamber. The discharge chamber 130 has an annular cross section with a central opening large enough to accommodate the conduit 150. The discharge chamber typically has a small diameter ("x" in FIG. 3) of about 2–10 cm, a large diameter ("y" in FIG. 3) of about 5–25 cm, and an axial length of about 5–25 cm. The discharge chamber 130 is typically filled with an ionizable gas which includes mercury and a buffer gas such as krypton, argon, or neon. The discharge chamber 130 may include an exhaust tube 132 which is used to fill the discharge chamber 130 with the ionizable gas. The mercury vapor pressure is typically 4–7 milliTorr, more typically about 6 milliTorr, while the vapor pressure of the rare gas is typically 0.1–10 Torr. A mercury vapor pressure of 6 milliTorr generally results in an efficient energy conversion from the electric field generated by the coil 110 to the 254 nanometer (nm) UV radiation emitted by the mercury atom. The rare gas reduces the mean free path of the electrons, which increases the instances of electrons colliding with Hg atoms.

To maintain a desired mercury vapor pressure, for example if the lamp is to be operated at high temperatures, an amalgam may be provided in the chamber 130 in the form of a pellet. The amalgam may comprise, for example, Bi and In; Pb, Bi, and Sn; Zn; Zn, In, and Sn; or In. The amalgam controls mercury vapor pressure by absorbing and releasing mercury in its gaseous phase in varying amounts, depending on the temperature. Each amalgam has its own optimum range of operating temperatures, as is known in the art. Such amalgams are described, for example, in U.S. Pat. No. 5,434,482.

The discharge chamber 130 may also include a composition for absorbing impurities inside the chamber. For example, as shown in FIG. 1, the composition 134 may comprise a conventional triphosphor blend or a halophosphate phosphor which is applied to one of the inside annular end surfaces of chamber 130. Alternatively, the composition may comprise a getter inserted into the chamber in the form of a strip which is heated and evaporates and deposits on the wall of the chamber. Getters are available commercially, for example from SAES Getters USA Inc. in Colorado Springs, Colo. A suitable getter from SAES Getters USA Inc. is referred to as St 101, and comprises 16 weight percent Al, and 84 weight percent Zr.

The discharge chamber 130 is typically formed of quartz, e.g. GE 021 Quartz or GE 214 Quartz produced by General Electric Company. Quartz, as opposed to glass, provides enhanced resistance to thermal stress, thus allowing the lamp to be operated at higher powers. Quartz can also provide better transmission in the UV wavelengths than glass. For example, at 254 nm, GE 982 Glass, which is specially doped to increase its UV transmission, has a transmittance of about 70% (2 mm sample); whereas GE 021 Quartz has a transmittance of about 92% (1 mm sample) and GE 214 Quartz has a transmittance of about 87% (1 mm sample).

FIG. 1 also shows a conduit 150 for carrying water or other fluid through the lamp. Typically, the UV radiation penetrates about 2–4 cm into water. Thus, the inner diameter of the conduit 150 is typically about 2–8 cm. The conduit 150 may have a wall thickness of 0.5–2.0 mm, for example. The conduit 150 comprises a material which has good transmission in the UV wavelengths. Typically, the conduit comprises quartz, e.g. GE 214 Quartz or GE 021 Quartz, which is transparent to UV radiation and which does not degrade significantly as a result of exposure to UV radiation. The conduit 150 may include suitable fixtures (not shown) at each end to connect the disinfection system to the desired water system.

In operation, the AC input voltage is converted by the rectifier into a DC voltage. The DC voltage is input to the oscillator which converts the DC voltage into an RF signal having the desired frequency and power. The RF signal is applied to the single turn coil 110 through the matching network to generate a magnetic field which in turn produces an electric field inside the chamber 130. The electric field inside the chamber 130 ionizes the contained gas, resulting in a UV emission as the excited mercury atoms return to the ground state. FIG. 1 shows a UV discharge 136 formed inside the discharge chamber 130 during operation. The UV discharge is generally torroidal in shape, as shown in FIG. 1. The UV emission propagates initially in all directions, but is reflected radially inwardly to the conduit 150 by the reflective coil 110. The discharge chamber may also be coated on its outer surface with a UV reflective material, e.g. in the form of a thin film, to reflect UV radiation back to the conduit 150.

Typically, the UV discharge has a wavelength of 254 nm, produced primarily by transition of the mercury atom from the $6^3P_1$ state to the ground state. This wavelength is very close to the wavelength of UV radiation, 260 nm, which is most effective at killing bacteria. Typically, the UV emission of the system is between 230 and 320 nm; however, other wavelengths can be used as desired.

Figure 4:
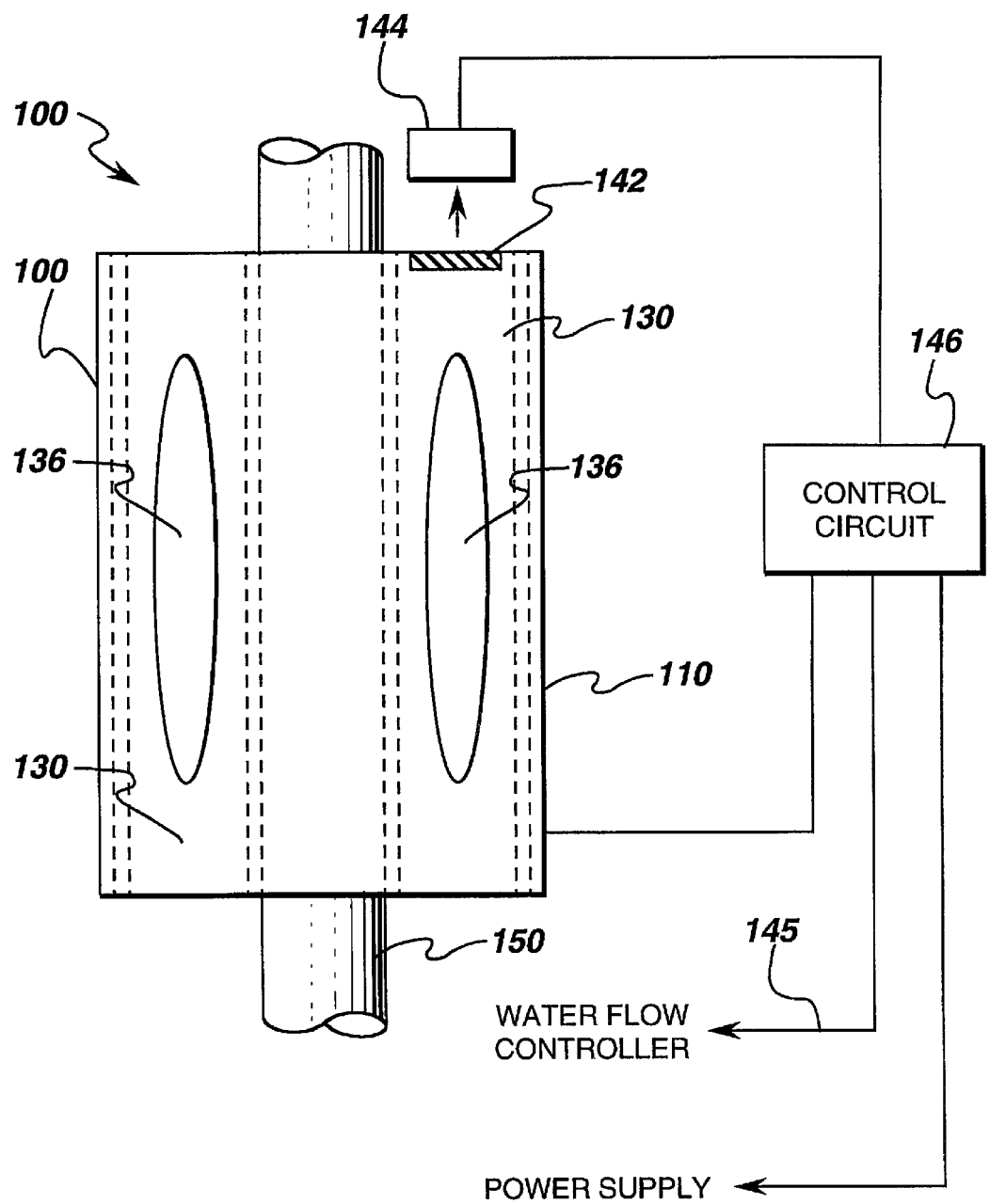
FIG. 4 is a drawing of a control system for the fluid irradiation system according to an exemplary embodiment of the invention.

FIG. 4 shows a detection system which can be used in conjunction with the disinfection system. A phosphor 142 is applied to a portion of the discharge chamber 130 exposed to a relatively low level of UV radiation. Visible light is generated when the phosphor (which may also function to absorb impurities) is exposed to UV radiation, as is well known in the art. The visible light is detected by a photocell 144. Alternatively, a photocell 144 may be provided which directly detects UV radiation without the use of a phosphor. Such a photocell is described, for example, in D. M. Brown et al., "Silicon Carbide UV Photodiodes", 40 IEEE Transactions on Electronic Devices 325–333 (1993), hereby incorporated by reference. The photocell 144 generates a signal, indicative of the light intensity, which is coupled to a control circuit 146. The control circuit 146 receives the signal from the photocell 144, and is adapted to respond in a desired manner. For example, the control circuit 146 can send a signal via line 145 to a flow controller to control the water flow so that a desired UV exposure is achieved. Alternatively, the control circuit 146 can send a signal via line 145 to the flow controller to shut off the water if the light intensity drops below a predetermined acceptable value. The control circuit 146 can also be designed to generate a feedback signal to be transmitted to the power supply 112 for the coil 110 to control the power supplied to the coil 110, e.g. to maintain a constant UV flux.

The dimensions of the lamp 100 can be chosen to achieve a desired degree of exposure of the fluid to the UV radiation at a desired flow rate. The amount of energy to which a certain volume of water is exposed can be calculated by dividing the lamp power by the flow rate and multiplying the result by the efficiency with which the lamp converts input electric energy to output UV energy. For example, a disinfection system operating at a lamp power of 100 watts, an efficiency of 60%, and a flow rate of 1.0 liter per second will expose each liter of water to 60 joules of UV radiation. Because the lamp according to exemplary embodiments of the invention can operate at relatively high powers, e.g. 200, the flow rate through the conduit 150 can be higher than the flow rate in conventional low power systems, while maintaining the same energy per volume exposure. Alternatively, the amount of energy exposure can be increased over the energy exposure in conventional systems while maintaining the same flow rate as in the conventional system.

The invention provides additional advantages over conventional UV water disinfection systems. For example, the lamp has no electrodes which results in a longer lifetime since conventional electrodes eventually run out of the alkaline earth oxide material which is used to sustain a sufficient level of thermionic emission of electrons. Thus, a lamp according to exemplary embodiments of the invention will typically not need to be replaced every 9–12 months, as is common in conventional systems.

The electrodeless design of the lamp also provides the advantage that there are no electrical leads passing through the walls of the chamber 130. Consequently, the chamber 130 can be easily made of quartz, which is much less susceptible to solarization and has good UV transmission properties, without the difficulty of sealing the electrodes.

Another advantage provided by exemplary embodiments of the invention is the ability to easily install multiple lamps to achieve the desired power for a system. For example, due to the compact design, the conduits 150 of several lamps can be connected end to end to enhance the disinfection capabilities of the system. By contrast, conventional systems employing an elongated lamp at lower power are more cumbersome to install due to their size and shape.

Figure 5:
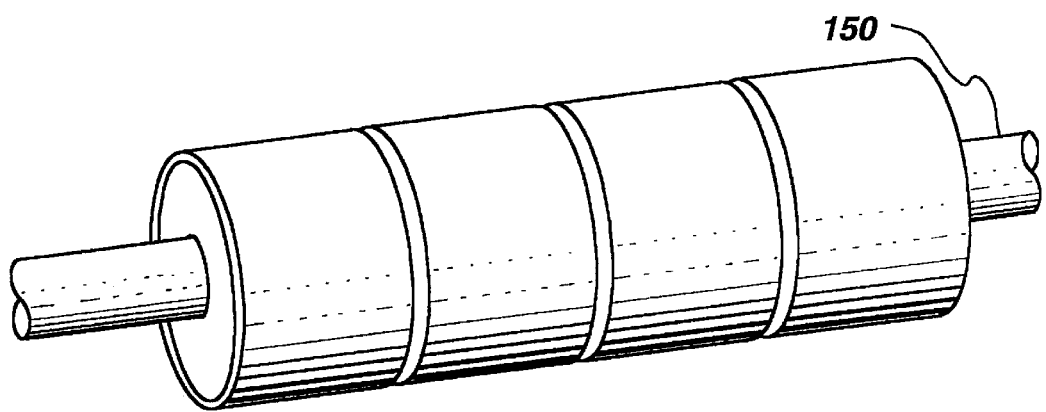
FIG. 5 is a drawing of a detection system which can be used in conjunction with the irradiation system according to another embodiment of the invention.

According to another embodiment of the invention shown in FIG. 5, a plurality of lamps, each including a coil 110 and discharge chamber 130, can be assembled in series along a single quartz conduit 150. In this way, a disinfection system can be configured such that a single quartz conduit 150 is serviced by multiple lamps. This configuration provides the advantage that a single conduit 150 can be easily removed for cleaning, rather than removing a conduit for each lamp. The ability to easily clean the conduit 150 may be an important advantage, particularly when the fluid to be disinfected is highly contaminated.

Figure 6:
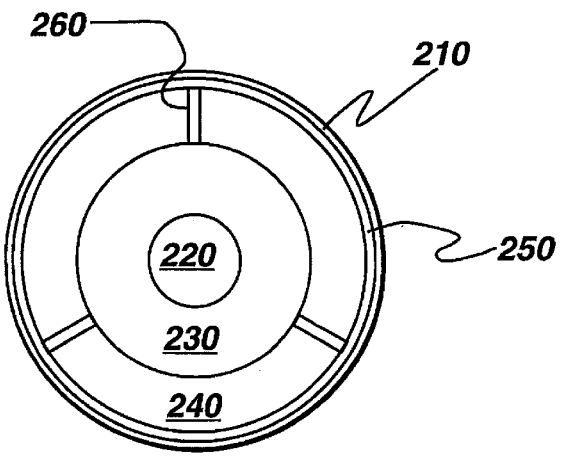
FIG. 6 is a drawing of a fluid irradiation system according to another embodiment of the invention.
Figure 7:
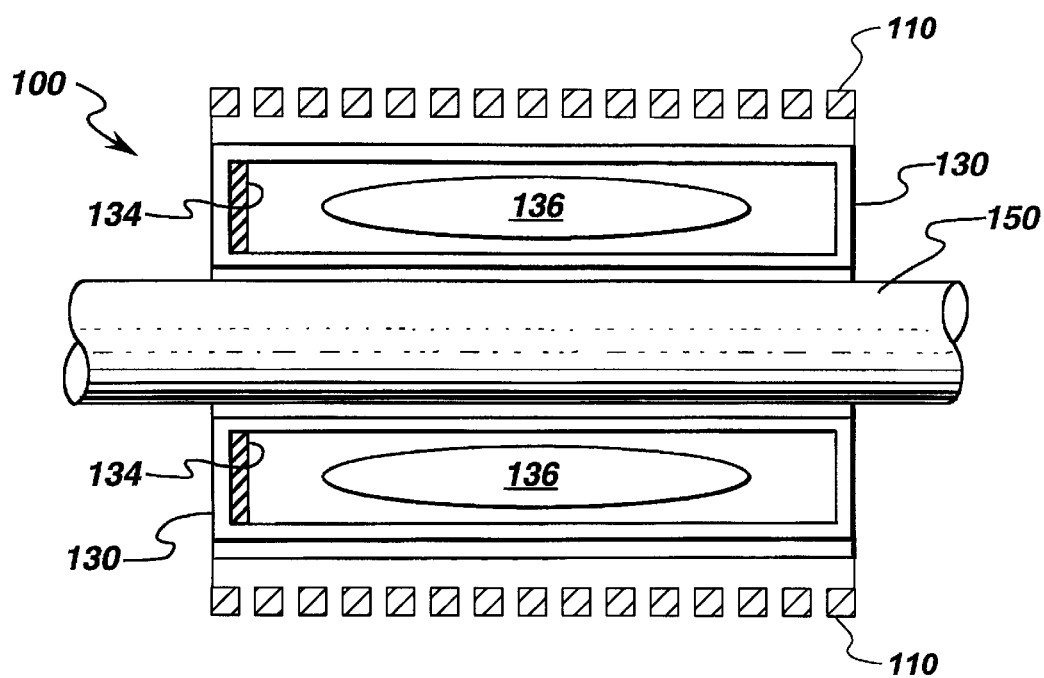
FIG. 7 is a cross sectional view of a fluid irradiation system comprising a multiple-turn coil according to an exemplary embodiment of the invention.

According to another embodiment of the invention shown in FIG. 6, the chamber 230 is installed within the conduit 250, and the drive coil 210 is mounted on the conduit 250. The chamber 230 can be designed such that its outer diameter is smaller than the inner diameter of the conduit 250, which leaves a space 240 between the chamber 230 and the conduit 250. In operation, water in the conduit 250 flows through the center 220 of the chamber 230 and around the outside 240 of the chamber 230. The chamber 230 can be fixed in place with any suitable supports 260.

Although the invention has been described with reference to exemplary embodiments, various changes and modifications can be made without departing from the scope and spirit of the invention. These and other modifications are intended to fall within the scope of the invention, as defined by the following claims.

What is claimed is:

1. An irradiation system comprising:

a conduit which is transparent to ultraviolet radiation;

a chamber having an annular cross section and being disposed around the conduit, the chamber containing an ionizable gas; and a coil, disposed around the chamber, for ionizing the ionizable gas to produce in the chamber an ultraviolet emission which propagates into the conduit.

2. The system of claim 1, wherein the coil is a single-turn metal coil.

3. The system of claim 1, wherein the coil is a multiple-turn coil.

4. The system of claim 1, wherein the coil is generally cylindrical in shape, and a ratio of the axial length of the coil to the diameter of the coil is less than or equal to 2.0.

5. The system of claim 1, wherein the conduit comprises quartz.

6. The system of claim 1, wherein the conduit, having a 1 millimeter wall thickness, has a transmittance of at least 87 percent of 254 nanometer radiation.

7. The system of claim 1, wherein the chamber comprises quartz.

8. The system of claim 1, wherein the chamber has a transmittance of at least 87 percent of 254 nanometer radiation for a chamber wall thickness of 1 millimeter.

9. The system of claim 1, further comprising a UV reflective coating on a surface of the chamber, which coating reflects UV radiation toward the conduit.

10. The system of claim 9, wherein the UV reflective coating is disposed on an outer surface of the chamber.

11. The system of claim 1, further comprising a power supply which supplies at least 50 watts to the coil.

12. The system of claim 1, further comprising a power supply which supplies at least 100 watts to the coil.

13. The system of claim 1, further comprising a power supply which supplies at least 150 watts to the coil.

14. The system of claim 1, wherein the ionizable gas comprises mercury and at least one of argon, neon, and krypton.

15. An irradiation apparatus comprising:

a coil for ionizing an ionizable gas; and a discharge chamber, containing the ionizable gas, disposed inside the coil, the discharge chamber having an annular cross section such that a cylindrical opening is provided through the discharge chamber, the cylindrical opening being fluidly isolated from the discharge chamber.

16. An irradiation apparatus comprising:

a conduit which is transparent to ultraviolet radiation; and a plurality of electrodeless lamps disposed around the conduit, each of the electrodeless lamps including a coil and a discharge chamber disposed within the coil, the discharge chamber containing an ionizable gas.

17. The apparatus of claim 16, wherein each of the discharge chambers has an annular cross section.

18. The apparatus of claim 17, wherein the lamps are adapted to allow the conduit to slide out of the lamps.

19. The apparatus of claim 18, wherein the conduit comprises quartz.

20. The apparatus of claim 18, wherein the discharge chambers comprise quartz.

21. An irradiation method comprising the steps of:
disposing a chamber around a conduit, the chamber including an annular cross section and containing an ionizable gas;
disposing a coil around the chamber for ionizing the ionizable gas;
disposing a conduit passing through the chamber, the conduit being fluidly isolated from the chamber;
generating a UV emission in the chamber; and flowing a fluid through the conduit such that the fluid is exposed to the UV emission generated in the chamber.

22. The method of claim 21, wherein the step of generating a UV emission comprises applying power to a coil disposed around the chamber.

23. The method of claim 22, wherein the coil is a cylindrical single turn coil.

24. The method of claim 22, wherein the step of generating a UV emission comprises applying a power of at least 100 watts to the coil with a power supply.

25. The method of claim 21, further comprising the step of reflecting UV radiation generated in the chamber toward the conduit.

26. The method of claim 25, wherein the UV radiation is reflected by the coil.

27. The method of claim 25, wherein the UV radiation is reflected by a UV reflective coating applied to the chamber.

28. The method of claim 21, wherein at least one of the conduit and the chamber are formed of quartz.

* * * * *